(12) United States Patent
Gallagher

(10) Patent No.: US 8,461,996 B2
(45) Date of Patent: Jun. 11, 2013

(54) INFANT MONITOR

(76) Inventor: Gregory J. Gallagher, Cape Town (ZA)

( * ) Notice: Subject to any disclaimer, the term of this patent is extended or adjusted under 35 U.S.C. 154(b) by 503 days.

(21) Appl. No.: 12/526,590

(22) PCT Filed: Feb. 8, 2008

(86) PCT No.: PCT/IB2008/050459
§ 371 (c)(1),
(2), (4) Date: Mar. 15, 2010

(87) PCT Pub. No.: WO2008/096328
PCT Pub. Date: Aug. 14, 2008

(65) Prior Publication Data
US 2010/0201524 A1  Aug. 12, 2010

(30) Foreign Application Priority Data
Feb. 9, 2007 (ZA) ........................ 07/1172

(51) Int. Cl.
*G08B 23/00* (2006.01)
(52) U.S. Cl.
USPC ............... 340/573.1; 340/539.12; 600/484; 600/534; 600/535; 600/595
(58) Field of Classification Search
USPC ........... 340/573.1, 539.12; 128/863; 600/534, 600/535, 595, 484
See application file for complete search history.

(56) References Cited

U.S. PATENT DOCUMENTS

| | | | |
|---|---|---|---|
| 4,576,179 A | | 3/1986 | Manus et al. |
| 4,696,307 A | * | 9/1987 | Montgieux ............... 600/534 |
| 5,295,490 A | * | 3/1994 | Dodakian ............... 600/534 |
| 5,469,143 A | * | 11/1995 | Cooper ............... 340/575 |
| 5,611,349 A | * | 3/1997 | Halleck et al. ............... 600/534 |
| 6,356,203 B1 | * | 3/2002 | Halleck et al. ............... 340/689 |
| 6,498,652 B1 | * | 12/2002 | Varshneya et al. ............ 356/477 |
| 6,794,990 B2 | * | 9/2004 | Tseng ............... 340/584 |
| 6,975,230 B1 | * | 12/2005 | Brilman ............... 340/573.1 |

(Continued)

FOREIGN PATENT DOCUMENTS

| | | |
|---|---|---|
| RU | 3536 | 2/1997 |
| SU | 363496 A1 | 12/1972 |
| WO | WO-2004/089202 A1 | 10/2004 |
| WO | WO-2005/011491 A1 | 2/2005 |

OTHER PUBLICATIONS

Extract from radioyania.ru which shows details of a Philips SCD 530 baby monitor; http://www.radionyania.ru/view_502.htm; May 12, 2011.

(Continued)

*Primary Examiner* — Benjamin C Lee
*Assistant Examiner* — Quang D Pham
(74) *Attorney, Agent, or Firm* — Novak Druce Connolly Bove + Quigg LLP

(57) ABSTRACT

A method and device (10) are provided for monitoring regular movement of a human body (34), such as an infant's body. The method includes attaching the device (10) to the body (34) with a protuberance (24) of the body in abutment with the body, so that the protuberance is deflected as the body moves regularly. The deflection of the protuberance (24) is monitored and an alarm (18,19,20,52) is activated if the pattern of deflection of the protuberance changes to a predetermined extent, e.g. if it is disrupted.

19 Claims, 4 Drawing Sheets

U.S. PATENT DOCUMENTS

| | | | |
|---|---|---|---|
| 7,034,690 B2* | 4/2006 | Chaco | 340/573.1 |
| 7,800,505 B2* | 9/2010 | Pietersen | 340/573.1 |
| 2002/0017997 A1* | 2/2002 | Felkowitz | 340/573.1 |
| 2002/0057202 A1* | 5/2002 | Luzon | 340/573.1 |
| 2002/0097155 A1* | 7/2002 | Cassel et al. | 340/573.1 |
| 2002/0124295 A1* | 9/2002 | Fenwick et al. | 2/69 |
| 2002/0196141 A1* | 12/2002 | Boone et al. | 340/540 |
| 2004/0261180 A1* | 12/2004 | Birns | 5/655 |
| 2005/0088296 A1* | 4/2005 | Lee | 340/539.12 |
| 2005/0215844 A1* | 9/2005 | Ten Eyck et al. | 600/22 |
| 2005/0215845 A1* | 9/2005 | Mahony et al. | 600/22 |
| 2005/0277842 A1* | 12/2005 | Silva | 600/534 |
| 2007/0043304 A1 | 2/2007 | Katayama | |
| 2008/0015457 A1* | 1/2008 | Silva | 600/534 |
| 2008/0094226 A1* | 4/2008 | O'Shea et al. | 340/573.1 |
| 2008/0150730 A1* | 6/2008 | Hsu | 340/573.1 |
| 2008/0167573 A1* | 7/2008 | Stivoric et al. | 600/549 |
| 2008/0183029 A1* | 7/2008 | Mackin et al. | 600/22 |
| 2008/0183095 A1* | 7/2008 | Austin et al. | 600/534 |
| 2008/0214949 A1* | 9/2008 | Stivoric et al. | 600/549 |
| 2008/0287745 A1* | 11/2008 | Hartmann | 600/300 |
| 2008/0300499 A1* | 12/2008 | Strube | 600/527 |
| 2009/0018421 A1* | 1/2009 | Sarussi et al. | 600/324 |
| 2009/0025728 A1* | 1/2009 | Aljuri et al. | 128/207.14 |
| 2009/0163778 A1* | 6/2009 | Sommerville | 600/301 |
| 2010/0109875 A1* | 5/2010 | Ayon et al. | 340/573.1 |
| 2010/0241018 A1* | 9/2010 | Vogel | 600/511 |
| 2010/0283617 A1* | 11/2010 | Huang et al. | 340/573.5 |
| 2010/0286567 A1* | 11/2010 | Wolfe et al. | 600/587 |
| 2010/0328075 A1* | 12/2010 | Rahamim et al. | 340/573.1 |
| 2011/0221598 A1* | 9/2011 | Eschler et al. | 340/575 |

OTHER PUBLICATIONS http:://www.usa.philips.com/c/avent-baby-health-monitoring/scd530_00/prd/en/; Nov. 17, 2011.

* cited by examiner

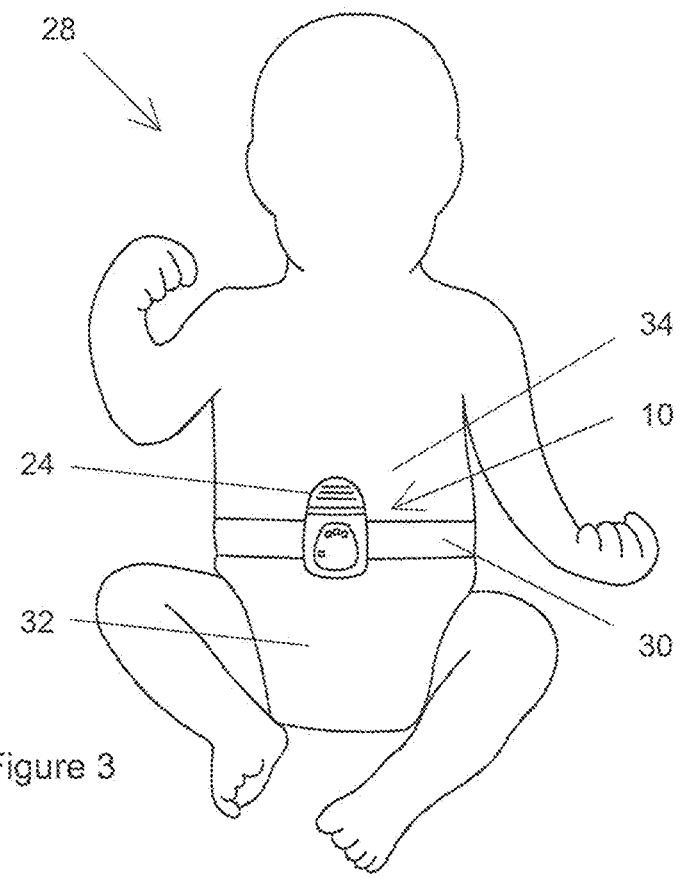
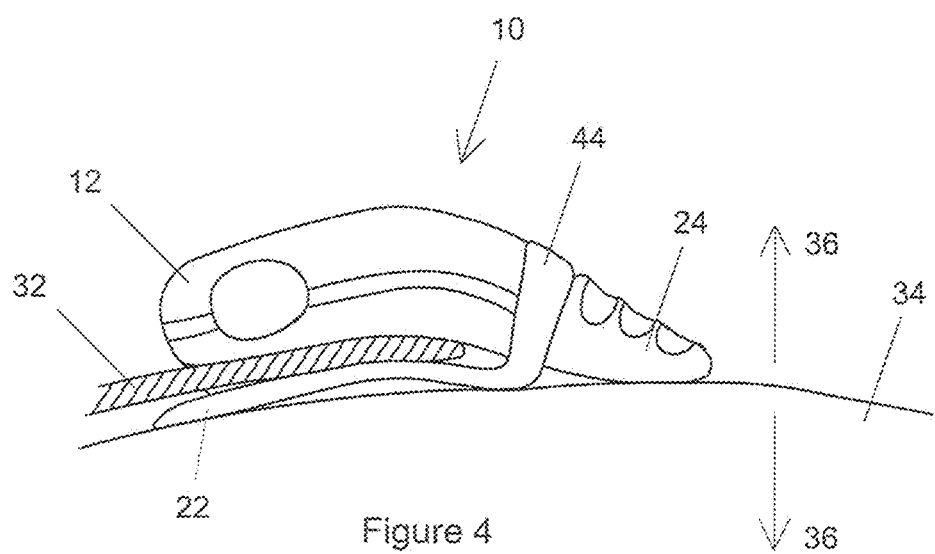

INFANT MONITOR

CROSS REFERENCE TO RELATED APPLICATIONS

This application is a national stage application (under 35 U.S.C. §371) of PCT/IB2008/050459, filed Feb. 8, 2008 which claims benefit of South African application 2007/01172 filed Feb. 9, 2007.

FIELD OF THE INVENTION

THIS INVENTION relates to the monitoring of conditions of the human body. In particular, the invention relates to a device and a method for monitoring movement of the body of a subject such as an infant, to monitor breathing, heartbeat, body temperature, and the like.

BACKGROUND TO THE INVENTION

Devices have been developed to monitor different conditions of the human body, especially infants' bodies, to alert childminders or caretakers to changes in physical conditions of the infants, e.g. disruptions of movements of the infants' bodies which could indicate that the infants' breathing and/or their heartbeats may have been disrupted, changes in humidity which could indicate a wet diaper, changes in temperature which could indicate a fever or that an infant is too hot or cold, and the like.

The purposes of such devices could be to draw attention of a childminder or caretaker to conditions which may require attention and/or to prompt the infant to resume breathing, or the like. One of the purposes for which such monitoring devices are intended, is to detect and address apnoea which may result in Sudden Infant Death Syndrome (SIDS) in infants.

A number of prior art monitoring devices are described by reference in International Patent Application No. PCT/ZA2004/000091, as well as an improved monitoring device which includes a clip for attaching the device to the waistband of an item of clothing and which has a pressure transducer located between the item of clothing and the skin, for monitoring breathing. However, in practice, the changes in pressure exerted on such a pressure transducer by movement of a breathing infant's body, are quite small since the position of the monitor is in a zone of low movement and pressure changes are subject to some uncontrollable factors such as diaper tightness and shrinking of the infant's body as it passes fluids and/or stool while sleeping. These factors make it difficult to detect breathing reliably over a normal period of monitoring.

The present invention seeks to provide improved practical and reliable means for monitoring movements of a human body, especially an infant's body, to monitor breathing, heartbeat, body temperature, and the like.

SUMMARY OF THE INVENTION

According to one aspect of the present invention there is provided a device for monitoring regular movement of the body of a human subject such as an infant, said device comprising:
  electronic circuitry including at least one alarm;
  attachment means for releasably attaching the device to the subject's body;
  a resiliently flexible protuberance extending from the device; and
  a transducer connected to the electronic circuitry and being configured to detect deflection of the protuberance;
  wherein the attachment means and the protuberance are configured such that the protuberance abuts the body of the subject when the device is attached to the subject's body and wherein the circuitry is configured to activate the alarm in the event that a pattern of the detected deflection of the protuberance changes to a predetermined extent.

For the purposes of this specification, the term "abut" refers to any contact, whether direct or indirect and more particularly, in respect of the abutment of the protuberance against the subject's body, the term includes direct abutting contact between the protuberance and the subject's skin and also include indirect contact between the protuberance and the subject's body via clothing or the like.

The device may further include one or more sensors such as a pressure sensor, temperature sensor, humidity sensor or microphone, configured to monitor conditions of the subject such as its heartbeat or body temperature, to detect crying and/or to monitor whether or not the subject's environment is clean and dry. The circuitry of the device may be configured to activate the alarm in the event that any predetermined event is detected by these sensors, such as a significant disruption in heartbeat or change in body temperature, an increase in noise level (e.g. when the subject is crying) or an increase in humidity, possibly indicating that the subject requires a diaper change or a change of bedclothes.

The attachment means may include a clip that may be attachable to a diaper or like article of clothing and the protuberance may extend from the same side of the device as the clip, may extend from any part of the device towards the side on which the clip is disposed, or may extend in any other suitable way in a direction where it will contact the body of the subject, in use.

The electronic circuitry may include at lease one alarm that causes at least a part of the device to vibrate, at least one alarm that emits sound, at least one alarm that emits light, a display device, and/or at least one alarm that transmits a signal to another device, upon being activated, and/or any other form of alarm.

According to another aspect of the present invention there is provided a method of monitoring regular movement of the body of a human subject such as an infant, said method including:
  releasably attaching a monitoring device to the subject's body, with a protuberance of the device in abutting contact with the body of the subject;
  allowing regular movement of the subject's body relative to the monitoring device to be transferred to the protuberance, causing the protuberance to deflect; and
  activating an alarm if the pattern of deflection of the protuberance changes to a predetermined extent.

The protuberance may be kept in abutment with the subject's body in the anterior abdominal region of the subject, e.g. in the vicinity of the centre of the stomach.

The protuberance may preferably be kept generally in continuous contact with the subject's skin.

The change in the pattern of deflection could be that the interval between successive deflections of the protuberance exceeds a predetermined maximum period or is shorter than a predetermined minimum period, or other deviations from the pattern of regular deflections.

The method may include monitoring any one or more of conditions of the subject such as its heartbeat or body temperature, to detect crying and/or to monitor whether or not the subject's environment is clean and dry and may include activating the alarm in the event that any predetermined event is detected by these sensors, as mentioned above.

The attachment of the device to the subject's body may include attaching the device to a diaper or other article of clothing of the subject, e.g. by clipping the device onto said article of clothing.

The alarm may be directed to the subject, e.g. by way of a tactile alarm or stimulator, an audible alarm, or the like and/or may be directed to alert other persons, e.g. an audible alarm, a visible alarm, transmission of a signal to a remote device, a display, or the like.

BRIEF DESCRIPTION OF THE DRAWINGS

For a better understanding of the present invention, and to show how the same may be carried into effect, reference will now be made, by way of non-limiting example, to the accompanying drawings in which:

FIG. 3 is a schematic anterior view of an infant wearing the device of FIG. 1;

FIG. 4 is a side elevation of the device of FIG. 1, on the abdomen of an infant;

DETAILED DESCRIPTION OF THE DRAWINGS

Figure 1:
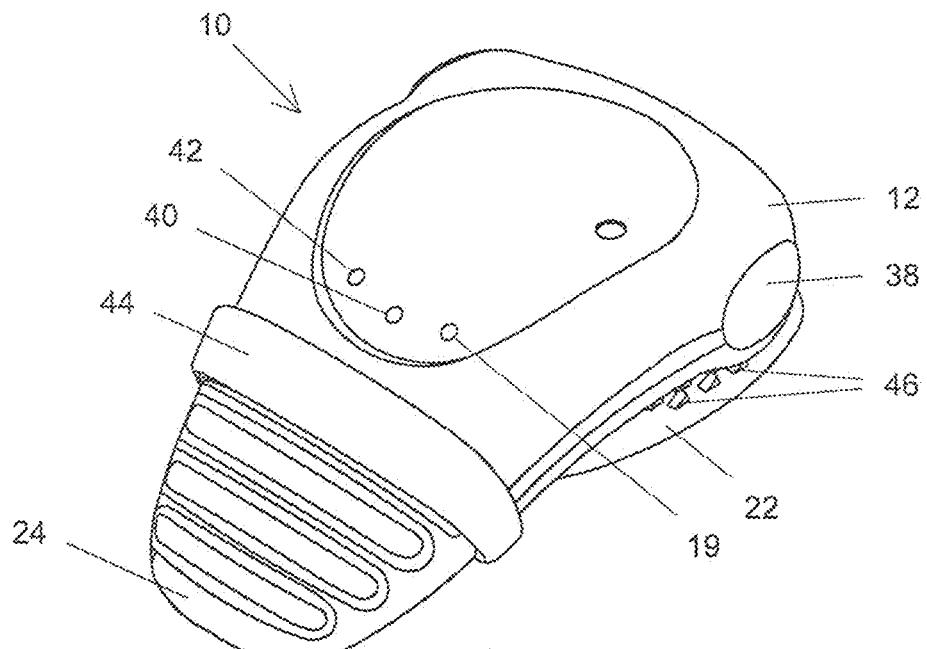
FIG. 1 is a top three dimensional view of a first embodiment of a monitoring device in accordance with the present invention.
Figure 2:
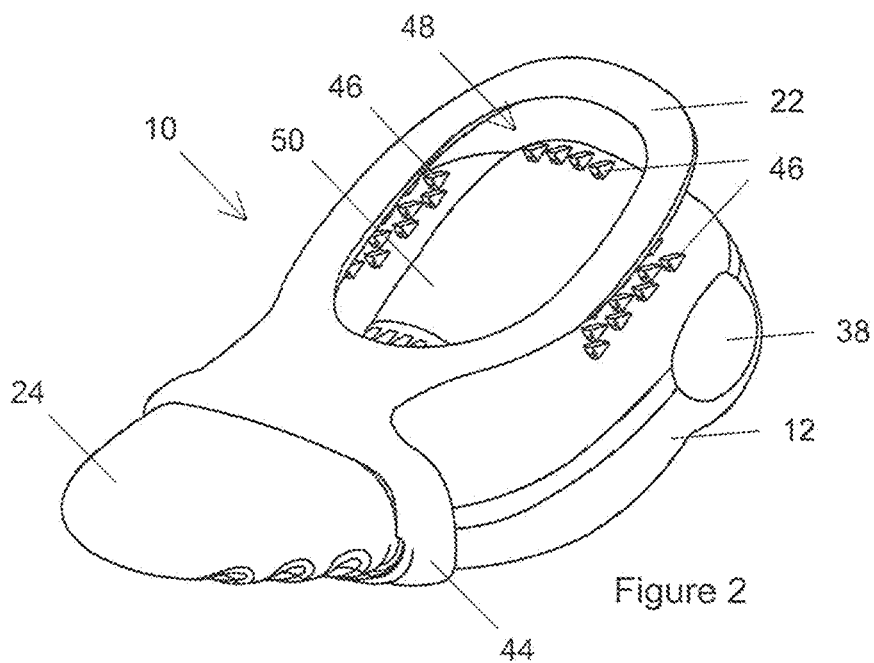
FIG. 2 is a bottom three dimensional view of the device of FIG. 1.
Figure 5:
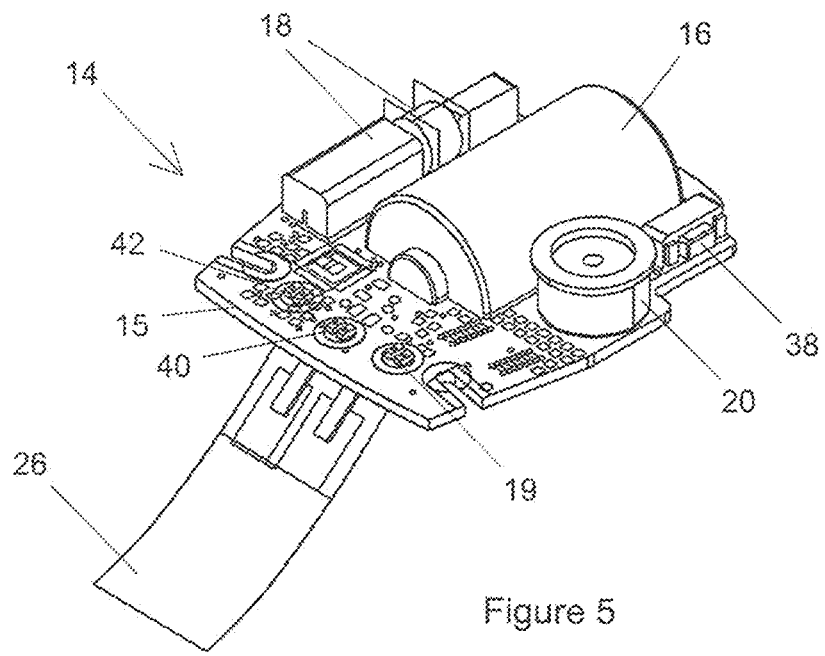
FIG. 5 is three dimensional view of internal electrical components of the device of FIG. 1.
Figure 6:
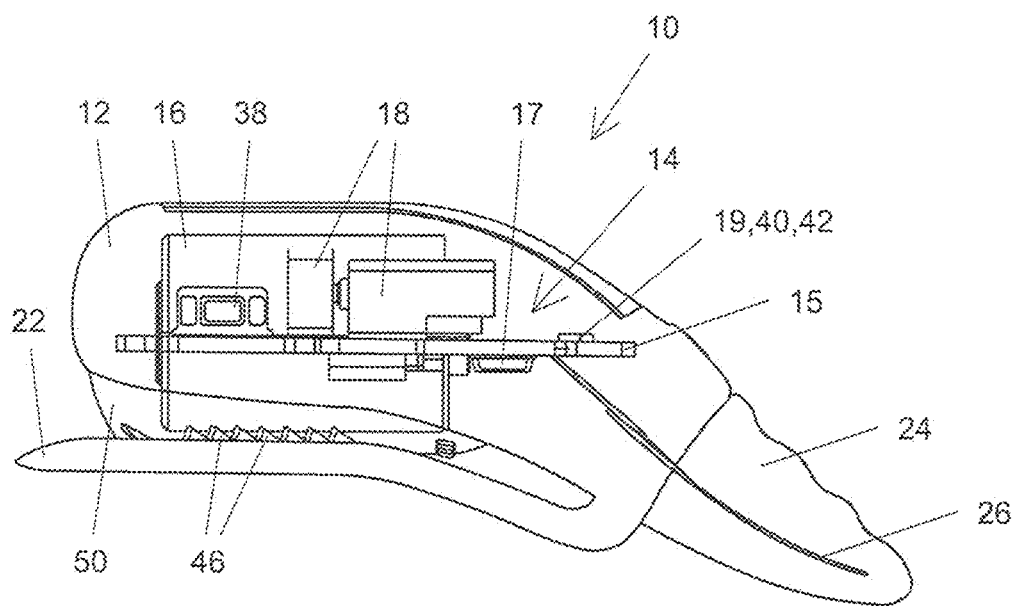
FIG. 6 is a part sectional side elevation of the device of FIG. 1.

Referring to the drawings, a monitoring device in accordance with the present invention is generally indicated by reference numeral 10. The same reference numerals are used to refer to like features in different embodiments of the device 10.

Referring to FIGS. 1 to 6, a first embodiment of the device 10 includes a casing 12 of a durable polymeric material that houses electronic circuitry 14 including a central processing unit (CPU), mounted on a circuit board 15, a power source in the form of a battery 16 configured to deliver electrical power to the circuitry and alarms in the form of a vibrator (or stimulator) 18, light emitting diodes (LED) 19 and a sound transducer or buzzer 20. These features of the device 10 are generally configured to perform similar functions to their counterparts described in International Patent Application No. PCT/ZA2004/000091.

The device 10 has buttons 38 on either side that can be operated to switch the device on an of and/or to change its modes of operation, and LEDs indicating battery power 40 and normal operation 42.

The device 10 has a clip 22 that extends from the underside of the casing 12 and that can be integrally formed with the casing, but that is attached to the casing by way of a collar 44 that extends around the casing. The clip 22 is configured to pinch parts of wearer's clothing (e.g. a baby's diaper) and in order to enhance its grip, protruding teeth formations 46 are provided on the clip 22 and on the casing 12 adjacent the clip. The clip 22 defines a central aperture 48 and the underside of the casing 12 defines a bulge 50, enhancing the grip on fabric extending between the clip 22 and the casing.

The device 10 further includes a protuberance 24 that extends from one end of the casing 12, adjacent the clip 22. The clip 22 and protuberance 24 are configured such that, when the device is clipped to an article of clothing worn by a subject, with the clip extending underneath the article of clothing, the protuberance is in abutting contact with the subject's body, directly onto its skin, or indirectly via clothes or the like. The protuberance 24 preferably extends from the device 10 at a slight angle, as can best be seen in FIGS. 4 and 6. It must however be appreciated that a wide variety of configurations of attachment means other than the clip 22 can be used and similarly, that the protuberance 24 can be configured quite differently, from the ribbed, tapering shape shown in the drawings.

The protuberance 24 is made of a flexible material such as a soft rubber that is much softer than the material of the casing 12 and clip 22, with the result that the protuberance can be deflected quite easily, but the material of the protuberance is sufficiently resilient to return to its normal position after being deflected. A transducer 26 extends inside the protuberance 24 and is configured to detect deflection of the protuberance and is connected to the circuitry 14 to signal to the electronics of the circuitry when the protuberance has been deflected. The transducer 26 can be a piezoelectric sensor or the like.

In use, when the movement of a human subject such as the infant 28 shown in FIG. 3 needs to be monitored in order to be alerted to apnoea, abnormal breathing, abnormal heart functioning, or the like, the device 10 is releasably attached to the body of the infant by clipping it to the waistband 30 of the infant's diaper 32, or like article of clothing, with the clip 22 extending underneath the diaper and with the protuberance in abutting contact with the infant's skin 34 on its stomach as shown in FIG. 4. It is to be appreciated that the protuberance 24 is deflected upwardly against its own resilience from its normal position as when placed in the position shown in FIG. 4. The result is that the resilience of the protuberance 24 urges it towards the skin 34, so that contact with the skin is generally maintained, mostly even if the diaper 32 is loose or becomes loose after being placed initially.

As the infant 28 breathes, the volume of its lungs vary at a regular, usually rhythmic rate, causing the anterior (upper) surface of its abdomen to move (rise and fall) in the directions indicated by reference numeral 36 in FIG. 4 and causes the curvature of the body or skin 34 to change. At the same time, the region below the waistband 30 and diaper 32, closer to the groin area, is less prone to movement and its movement is inhibited to some extent by the diaper. Accordingly, there is a relative movement between the part of the infant's body in contact with the clip 22 and the part in contact with the protuberance 24. It is to be appreciated that the infant 28 is shown in a prostrate position in FIGS. 3 and 4, in which the movement of the anterior surface of its abdomen is particularly noticeable, but the movements are also noticeable when the infant lies on its sides.

The relative movement of the skin 34 in the different regions and particularly the changes in the curvature of the skin across these regions, causes the protuberance 24 to be deflected relative to the rest of the device 10 in the directions 36 and the deflection of the protuberance is monitored by the transducer 26 and is conveyed to the circuitry 14. The circuitry 14 is configured to monitor the regular relative movement of the abdomen (via the protuberance 24 and transducer 26) and to activate one or more of the alarms if the regular movement changes by a predetermined amount.

The options of configurations of the circuitry to determine when an alarm needs to be activated are unlimited, but it can be configured to activate the alarm when the period between consecutive deflections of the protuberance 24 is longer than a predetermined time (possibly caused by apnoea) or is too short (possibly caused by hyperventilation or suffocation). Further, the circuitry can be configured with a degree of intelligence to anticipate the respiratory rhythm of a particular infant 28, to filter out or ignore anomalies when the infant sighs, yawns, or the like, without raising the alarm, etc.

When the circuitry 14 activates an alarm, it can activate the vibrator 18, LED 19 and/or sound transducer or buzzer 20, but in a preferred embodiment of the invention, the circuitry 14 is configured to activate the vibrator after detecting no breathing for approximately fifteen seconds and to activate the buzzer after detecting no breathing for approximately twenty seconds, although these predetermined parameters can be changed. The vibrator 18 can generally be positioned anywhere in the device 10 and if it is activated and vibrates, the vibrations are easily felt against the infant's skin 34. The vibration is intended to wake the infant 28 and/or to elicit a response, to overcome possible apnoea or other conditions such as SIDS, cessation of breathing events, movement, etc. The radiating LED 19 and sounding buzzer 20 are intended to draw the attention of a childminder or caretaker to tend to the infant 28.

Similarly to monitoring the movement of the abdomen to monitor the infant's 28 breathing, the protuberance 24 can be made sufficiently sensitive to detect movements on the abdomen caused by the heart beat of the infant and the circuitry can be configured to activate an alarm when the heart beat deviates from a normal, regular pattern, to a predetermined extent.

The device 10 and its use have been described with reference to a subject who is shown in the drawings as an infant 28, but it is to be understood that the device can also be used on adults, e.g. patients who are prone to respiratory disruptions while asleep, with suitable adjustments if necessary.

Figure 7:
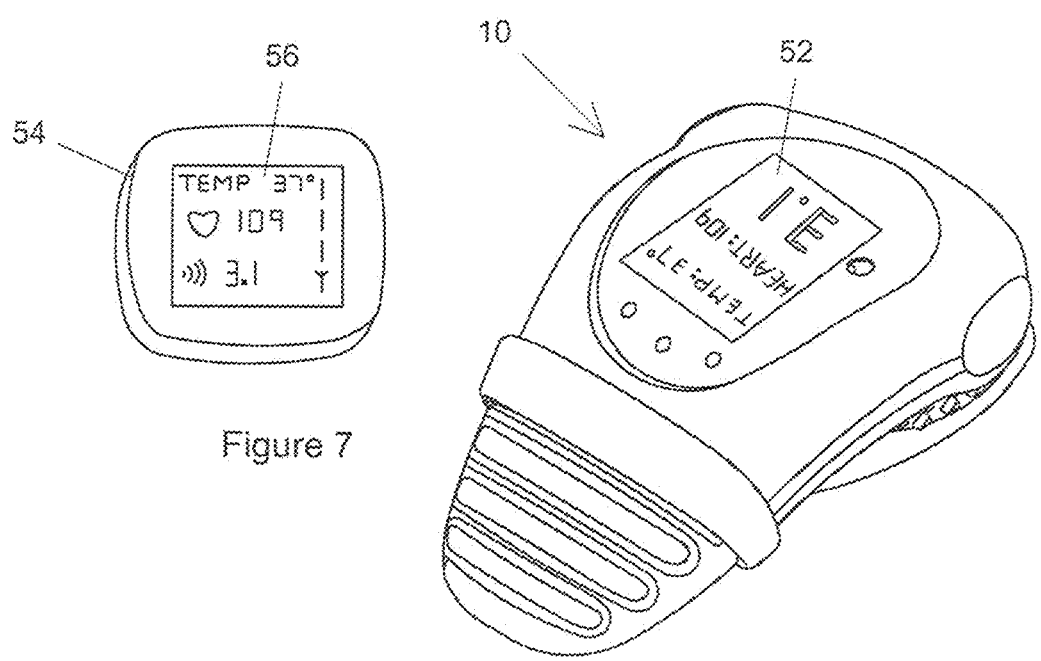
FIG. 7 is a top three dimensional view of a second embodiment of a monitoring device in accordance with the present invention, including a remote control unit.
Figure 8:
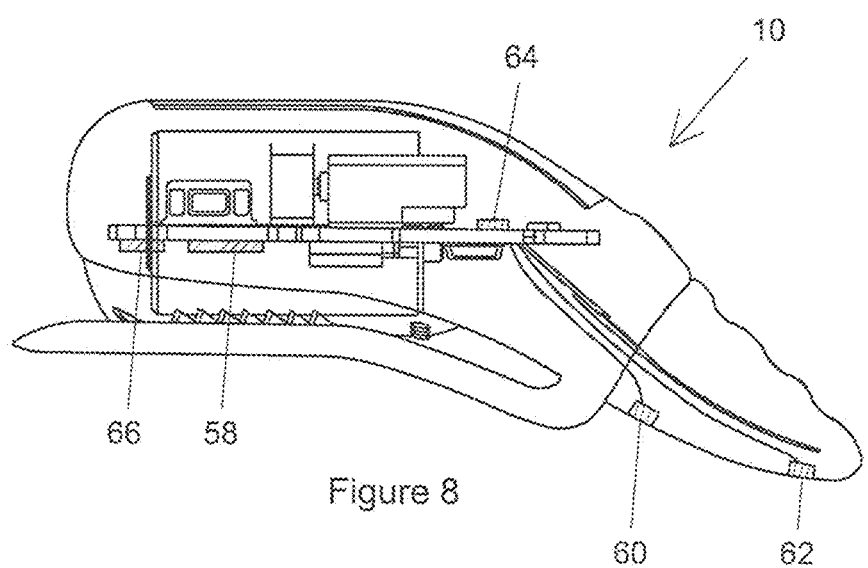
FIG. 8 is a part sectional side elevation of the monitoring device of FIG. 7.

Referring to FIGS. 7 and 8, in a second embodiment of the device 10, the device includes a display 52 in the form of a liquid crystal (LCD) display screen, which can be configured to display information of use to a minder of the subject, such as its hear rate, body temperature, alarm statuses, etc. Further, the device 10 can communicate wirelessly from a transceiver 58 with a remote unit 54, which can in turn include a display 56 and any of the other alarms mentioned in respect of the first embodiment of the device 10 shown in FIGS. 1 to 6.

The device includes a number of additional sensors in the form of a humidity sensor 60 to monitor the humidity in the vicinity of the infant and trigger the alarm (18,19,20,52) if an increase in humidity is sensed, which could indicate that the infant may have wet or soiled itself, a temperature sensor 62 disposed to monitor the infant's body temperature, a microphone 66 configured to detect when the infant is crying and a gyroscope or accelerometer 64 to monitor movement or the orientation of the infant.

In other embodiments of the invention, the protuberance 24 can extend from any part of the casing 12, e.g. from the top of the casing, at an angle that allows it to abut the skin of an infant. Further, the protuberance 24 can include a lip of relatively harder material and a softer flexible part between the lip and the casing, forming a resiliently flexible hinge.

The invention claimed is:

1. A device for monitoring regular breathing movement of the body of an infant, said device comprising:
    an electronic circuitry including at least one alarm; and
    an attachment means for releasably attaching the device to the infant body in the anterior abdominal region;
    characterised in that said device includes a resiliently flexible protuberance extending from the device; and
    a transducer connected to the electronic circuitry and extended inside said protuberance to detect deflection of the protuberance;
    said attachment means and protuberance being configured such that the protuberance abuts the body of the infant in the anterior abdominal region when the device is attached to the infant body in the anterior abdominal region and said electronic circuitry being configured to activate the alarm in an event that a pattern of the detected deflection of the protuberance changes to a predetermined extent.

2. The device as claimed in claim 1, characterised in that said device includes at least one sensor configured to monitor a condition, said electronic circuitry being configured to activate said alarm in the event that a predetermined event is detected by the at least one sensor.

3. The device as claimed in claim 2, characterised in that said at least one sensor includes a sensor selected from a temperature sensor, a humidity sensor and a microphone.

4. The device as claimed in claim 1, characterised in that said attachment means includes a clip that is attachable to an article of clothing of the infant.

5. The device as claimed in claim 4, characterised in that said protuberance extends from any part of the device towards the side on which the clip is disposed in a direction such that said protuberance abuts the body of the infant in the anterior abdominal region, in use.

6. The device as claimed in claim 1, characterised in that said electronic circuitry includes the alarm that is configured to cause at least a part of the device to vibrate.

7. The device as claimed in claim 1, characterised in that said electronic circuitry includes the alarm that is configured to emit sound.

8. The device as claimed in claim 1, characterised in that said electronic circuitry includes the alarm that is configured to emit light.

9. The device as claimed in claim 1, characterised in that said electronic circuitry includes the alarm that is configured to transmit a signal to another device, upon being activated.

10. The device as claimed in claim 2, characterised in that said attachment means includes a clip that is attachable to an article of clothing of the infant.

11. The device as claimed in claim 2, characterised in that said electronic circuitry includes the alarm that is configured to cause at least a part of the device to vibrate.

12. A method of monitoring regular breathing movement of the body of an infant, said method including:
    releasably attaching a monitoring device to the infant body in the anterior abdominal region, with a protuberance of the device in abutting contact with the body of the infant in the anterior abdominal region;
    characterised by allowing regular movement of the infant body in the anterior abdominal region relative to the monitoring device to be transferred to the protuberance, causing the protuberance to deflect; and
    activating an alarm of the monitoring device if a pattern of deflection of the protuberance changes to a predetermined extent;
    wherein the monitoring device comprises a transducer connected an electronic circuitry and extended inside the protuberance to detect the pattern of deflection of the protuberance.

13. The method as claimed in claim 12, characterised by keeping said protuberance in abutment with the body of the infant in the anterior abdominal region.

14. The method as claimed in claim 12, characterised by keeping said protuberance generally in continuous contact with the infant's skin.

15. The method as claimed in claim 12, characterised in that said change in the pattern of deflection is that an interval between successive deflections of the protuberance exceeds a predetermined maximum period.

16. The method as claimed in claim 12, characterised in that said change in the pattern of deflection is that an interval between successive deflections of the protuberance is shorter than a predetermined minimum period.

17. The method as claimed in claim 12, characterised in that said method includes monitoring at least one condition of said infant selected from the infant's heartbeat, the infant's body temperature, crying, and humidity of said infant's environment, and said method includes activating the alarm in a predetermined event is detected in said monitored condition.

18. The method as claimed in claim 12, characterised in that said attachment of the monitoring device to the infant's body includes attaching the monitoring device to an article of clothing of the infant.

19. The method as claimed in claim 12, characterised in that said alarm includes at least one of a tactile alarm, an audible alarm, a visible alarm, a transmission of a signal to a remote device, or a display.

* * * * *